United States Patent
Porter

(10) Patent No.: US 7,977,526 B2
(45) Date of Patent: Jul. 12, 2011

(54) SIMULATED COUNTERCURRENT ADSORPTIVE SEPARATION PROCESS

(76) Inventor: John R. Porter, Friendswood, TX (US)

( * ) Notice: Subject to any disclaimer, the term of this patent is extended or adjusted under 35 U.S.C. 154(b) by 380 days.

(21) Appl. No.: 12/389,671

(22) Filed: Feb. 20, 2009

(65) Prior Publication Data

US 2009/0247806 A1   Oct. 1, 2009

Related U.S. Application Data

(66) Substitute for application No. 61/041,396, filed on Apr. 1, 2008.

(51) Int. Cl.
*C07C 7/12* (2006.01)

(52) U.S. Cl. ........ 585/828; 585/820; 585/826; 585/827; 585/829

(58) Field of Classification Search .......................... None
See application file for complete search history.

(56) References Cited

U.S. PATENT DOCUMENTS

| | | | |
|---|---|---|---|
| 3,201,491 A | 8/1965 | Stine et al. | |
| 4,029,717 A | 6/1977 | Healy et al. | |
| 4,961,881 A * | 10/1990 | Ou | 554/193 |
| 5,912,395 A | 6/1999 | Noe | |
| 7,208,651 B2 | 4/2007 | Frey | |

FOREIGN PATENT DOCUMENTS

WO   95/07740   3/1995

OTHER PUBLICATIONS

Broughton, D.B. et al., "*Adsorptive Separations by Stimulated Moving Bed Technology: The Sorbex Process*", Fundamentals of Adsorption-Proceedings of the Engineering Foundation Conference held at Schloss Elmau, Upper Bavaria, West Germany, May 6-11, 1983, pp. 115-134.
Broughton, D.B., et al., "*The Parex Process for Recovering Paraxylene*", Chemical Engineering Progress, 1970, vol. 66, No. 9, pp. 70-75.

* cited by examiner

*Primary Examiner* — Tam M Nguyen
(74) *Attorney, Agent, or Firm* — Andrew B. Griffis

(57) ABSTRACT

A process is described for the separation of a first chemical compound from a liquid feed stream comprising at least first and second chemical compounds by simulated countercurrent adsorptive separation. In the process, the feed stream and a liquid desorbent stream are passed into at least one multi-bed adsorbent chamber at two different points via different transfer lines and an extract stream rich in the first chemical compound and a raffinate stream depleted in the first chemical compound are removed from the adsorbent chamber at two different points by two additional transfer lines. In addition, the contents of the transfer line which has just been used to supply the desorbent stream are flushed into the adsorbent chamber at a point along the chamber between the transfer line just used to supply the desorbent stream and the transfer line just used to withdraw the raffinate.

5 Claims, 1 Drawing Sheet

SIMULATED COUNTERCURRENT ADSORPTIVE SEPARATION PROCESS

PRIORITY CLAIM

This application claims the benefit of U.S. Provisional Application No. 61/041,396, filed Apr. 1, 2008, the entirety of which is incorporated by reference.

FIELD

This invention relates to a simulated countercurrent adsorptive separation process particularly, but not exclusively, for separation of para-xylene from a mixture of xylene isomers.

BACKGROUND

Para-xylene is typically recovered from a predominantly $C_8$ aromatic hydrocarbon fraction derived from various sources, such as catalytic reforming, by liquid-liquid extraction and/or fractional distillation. The $C_8$ aromatic hydrocarbon fraction is normally subjected to xylene isomerization to increase the concentration of the desired para-isomer and the para-xylene is then separated from the resultant product stream, usually containing all three xylene isomers, by either crystallization or adsorptive separation or a combination of these two techniques. Adsorptive separation is the newer technique and has captured the great majority of the market share of newly constructed plants for the production of para-xylene.

Essentially all of these adsorptive separation units use a simulated countercurrent movement of the adsorbent and the xylene containing feed stream. This simulation is performed using established commercial technology wherein the adsorbent is held in place in one or more cylindrical adsorbent chambers and the positions at which the streams involved in the process enter and leave the chambers are slowly shifted along the length of the beds. Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals. Each shift in location of these transfer points delivers or removes liquid from a different bed within the chamber. This shifting could be performed using a dedicated line for each stream at the entrance to each bed. However, this would greatly increase the cost of the process and therefore the lines are reused and each line carries one of the four process streams at some point in the cycle.

The general technique employed in the performance of a simulated moving bed adsorptive separation is well described in the open literature. For instance a general description directed to the recovery of para-xylene was presented at page 70 of the September 1970 edition of Chemical Engineering Progress (Vol. 66, No 9). A generalized description of the process with an emphasis on mathematical modeling was given at the International Conference on "Fundamentals of Adsorption", Schloss Elmau, Upper Bavaria, Germany on May 6-11, 1983 by D. B. Broughton and S. A. Gembicki. U.S. Pat. No. 4,029,717 issued to F. J. Healy et al. describes a simulated moving bed adsorptive separation process for the recovery of para-xylene from a mixture of xylene isomers. Numerous other available references describe many of the mechanical parts of a simulated moving bed system, including rotary valves for distributing various liquid flows, the internals of the adsorbent chambers and control systems.

The prior art recognizes that the presence of residual compounds in the transfer lines can have detrimental effects on the simulated moving bed process. For example, U.S. Pat. No. 3,201,491 and International Patent Publication WO 95/07740 both address the flushing of the line used to deliver the feed stream to the adsorbent chamber as a means to increase the purity of the recovered extract or sorbate component. This step avoids contamination of the extract stream with raffinate components of the feed remaining in this line when it is subsequently used to withdraw the extract stream from the adsorbent chamber. Both references employ a desorbent rich steam to flush the contents of this line back into the adsorbent chamber.

In addition, U.S. Pat. No. 5,912,395 discloses that the capacity of a simulated moving bed adsorptive separation process can be increased by flushing the contents of the transfer line just previously used to remove the raffinate stream from the adsorbent chamber back into the adsorbent chamber. This flushing step is performed immediately upstream of the point of raffinate withdrawal and eliminates the passage of raffinate material into the adsorbent chamber when the transfer line is subsequently used to charge the feed stream to the adsorbent chamber. The flushing liquid is preferably the feed stream to the process.

In contrast, U.S. Pat. No. 7,208,651 discloses a simulated moving bed adsorptive separation process in which the contents of the transfer line previously used to remove the raffinate stream from the adsorbent chamber is flushed away from the adsorbent chamber into the raffinate column used to separate desorbent from raffinate product. The flushing liquid is a stream from the adsorbent chamber at an intermediate point between the feed entry point and raffinate withdrawal. This flushing step is intended to eliminate the passage of raffinate material into the adsorbent chamber in the transfer-line flush period or when the process conduit is subsequently used to charge the feed stream to the adsorbent chamber.

According to the present invention, a simulated moving bed adsorptive separation process is provided in which the contents of the transfer line just previously used to supply the desorbent stream to the adsorbent chamber is flushed into the adsorbent chamber. This flushing step is performed at an intermediate point along the column between the desorbent entry point and raffinate withdrawal point. The flushing liquid is conveniently the raffinate flush stream. This flushing step maximizes utilization of the desorbent and, by reducing the amount of unused desorbent flowing to the raffinate tower, reduces the energy requirements of the raffinate tower.

SUMMARY

In one aspect, the invention resides in a process for the separation of a first chemical compound from a liquid feed stream comprising at least first and second chemical compounds by simulated countercurrent adsorptive separation, the process comprising:

(a) passing the feed stream and a liquid desorbent stream into at least one multi-bed adsorbent chamber at two different points via different transfer lines;

(b) removing an extract stream rich in said first chemical compound and a raffinate stream depleted in said first chemical compound from the adsorbent chamber at two different points by two additional transfer lines; and (c) flushing the contents of the transfer line which has just been used to supply the desorbent stream into the adsorbent chamber at a point along the chamber between said transfer line just used to supply the desorbent stream and the transfer line just used to withdraw the raffinate.

Conveniently, the process further comprises:

(d) flushing the contents of the transfer line which has just been used to remove the raffinate stream from the adsorbent chamber and using at least part of the raffinate flush for said flushing (c).

Conveniently, a stream from the adsorbent chamber at an intermediate point between the feed entry point and raffinate withdrawal point is used for the flushing (d).

Conveniently, the volume of liquid used for said flushing (c) is from about 0.5 to about 1 times, such as about 0.85 to about 0.95 times, the total volume of said transfer line and associated valving.

In one embodiment, the feed stream comprises a $C_8$ aromatics hydrocarbon stream and said first chemical compound comprises para-xylene.

DETAILED DESCRIPTION OF THE EMBODIMENTS

Described herein is a simulated countercurrent adsorptive separation process for separating a first chemical compound from a liquid feed stream comprising a mixture of the first chemical compound with at least a second chemical compound. In particular, the present process is intended for use in separating para-xylene from a mixture of $C_8$ aromatic hydrocarbon isomers and, for convenience, the present process will be described in connection with this separation. It is, however, to be appreciated that the process is equally applicable to the separation of other mixtures.

Processes for the adsorptive separation of para-xylene from other xylene isomers by simulated countercurrent adsorption are both widely described and widely practiced. An example of such a commercial application is the Parex™ Process. These processes typically include at least four separate steps which are performed sequentially in separate zones within a mass of adsorbent arranged to selectively adsorb para-xylene over the other xylene isomers. Each of these zones is normally formed from a plurality of beds of adsorbent, sometimes referred to as sub-beds, with the number of beds per zone ranging from 2 or 3 up to 8-10. The most widely practiced commercial process units typically contain about 24 beds. All of the beds are contained in one or more vertical vessels referred to herein collectively as the adsorbent chamber. The beds are structurally separated from one another by horizontal liquid collection/distribution grids. Each grid is connected to a transfer line defining a transfer point at which process streams enter and leave the vertical adsorption chambers.

The process streams comprise (a) the feed composed of a mixture of $C_8$ aromatic hydrocarbon isomers; (b) a desorbent, normally para-diethylbenzene; (c) a raffinate stream comprising a para-xylene depleted mixture of $C_8$ aromatic hydrocarbon isomers and (d) an extract stream comprising a mixture of para-xylene and the desorbent. A valve system, typically comprising one or more rotary valves, cycles the incoming process streams (feed and desorbent) and the outgoing process streams (extract and raffinate) through the transfer lines to the appropriate sieve beds to simulate countercurrent flow between the adsorbent and the feed stream and between the adsorbent and the desorbent. Since each transfer line carries each process stream at some point in the cycle, the valve system also feeds various flush streams to and from the transfer lines so as to avoid contamination caused by the process streams previously carried by the transfer lines.

Figure 1:
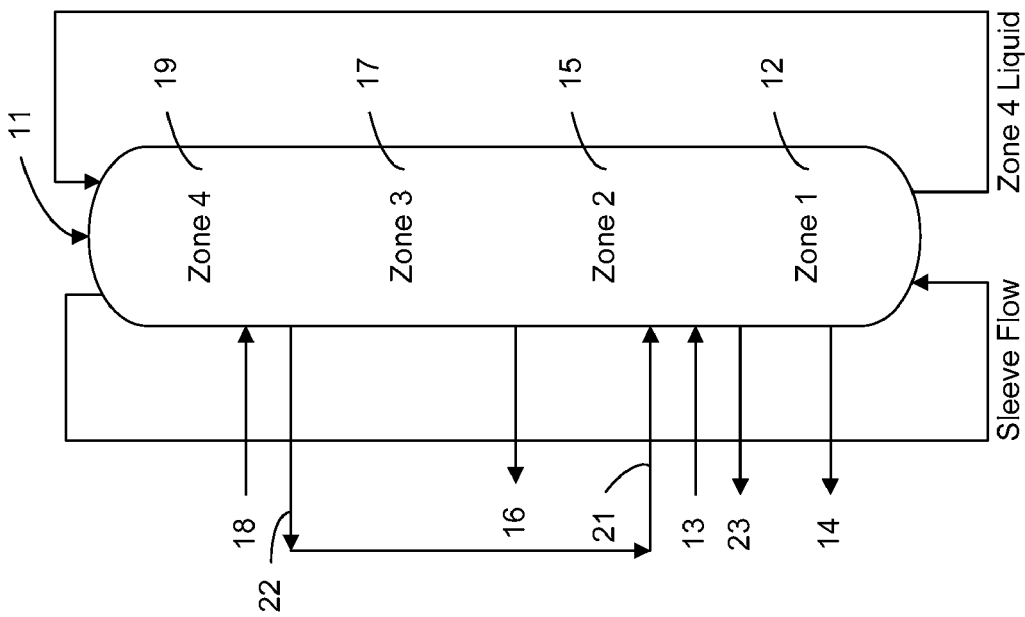
FIG. 1 is a schematic illustration of a conventional simulated countercurrent adsorptive separation system.

A schematic representation of a conventional simulated countercurrent adsorptive separation system is shown in FIG. 1. Referring to FIG. 1, the system includes a vertically disposed adsorbent chamber 11 which is divided into four zones by the position of the injection and withdrawal of the four process streams into and out of the chamber 11.

The first zone 12 is defined between the point of injection of the feed stream 13 and the point of withdrawal of the raffinate stream 14. As the feed stream 13 flows down through the first zone 12, countercurrent to the simulated upward flow of the solid adsorbent, the para-xylene is selectively adsorbed within the pores of adsorbent, leaving a para-xylene depleted liquid, which is partially removed as the raffinate stream 14.

The second zone 15 is defined between the point of injection of the feed stream 13 and the point of withdrawal of the extract stream 16. At the fresh injection feed point, the solid adsorbent contains the quantity of para-xylene that was adsorbed in the first zone 12. However, the pores will also contain a large amount of other xylene isomers, because the adsorbent has just been in contact with fresh feed. The liquid entering the top of the second zone 15 contains only para-xylene and desorbent. Due to the concentration gradient, as the adsorbent moves up through the second zone 15, the other xylene isomers are gradually displaced from the pores of the adsorbent by the preferentially adsorbed para-xylene and desorbent. Therefore, at the top of the second zone 15 the pores of the adsorbent contain only para-xylene and desorbent.

The third zone 17 is defined between the point of injection of the desorbent 18 and the point of withdrawal of the extract stream 16. The adsorbent entering the bottom of third zone 17 carries only para-xylene and desorbent, whereas the liquid entering the top of the third zone 17 consists of pure desorbent. As the liquid stream flows downward, the para-xylene in the pores of the adsorbent is displaced by the desorbent due to the concentration gradient. The liquid leaving the bottom of the third zone 17 is therefore composed of both para-xylene and desorbent. A portion of this liquid is withdrawn as the extract stream 16, while the remainder flows down into the second zone 15 as reflux.

The fourth zone 19 is where the para-xylene depleted liquid from the first zone is segregated from the extract stream 16 produced in the third zone 17. At the top of the third zone 17, the adsorbent pores are completely filled with desorbent. The liquid entering the top of the fourth zone 19 consists of para-xylene depleted liquid and desorbent. By properly regulating the flow rate into the fourth zone 19 it is possible to prevent the flow of the para-xylene depleted liquid into the third zone 17 and hence avoid contamination of the extract stream 16.

It is readily apparent that when a transfer line which is being used to transport a particular process stream is left idle at the end of a step it will remain full of the compounds forming that stream until these compounds are removed from the line by the next process stream. The residual compounds left in the now unused transfer line will therefore either be withdrawn from the process as the initial part of a process stream removed from the adsorbent chamber 11 or forced into the adsorbent chamber 11 when the transfer line carries a stream to be passed into the adsorbent chamber. The presence of these residual compounds in the transfer lines can have detrimental effects on the performance of the separation process and hence most existing processes employ flushing of the transfer lines at certain stages in the cycle.

In the system shown in FIG. 1, the contents of the transfer line used to deliver the feed stream 13 to the adsorbent chamber 11 are flushed into the chamber 11 to avoid contamination of the extract stream 16 with the raffinate components of the feed remaining in this line when it is subsequently used to withdraw the extract stream 16 from the adsorbent chamber 11. The feed flush stream is shown at 21. Similarly, the contents of the transfer line used to remove the extract stream 16 from the adsorbent chamber 11 are flushed away from the chamber 11 in order to prevent the desorbent pushing the contents back into the chamber 11 at a point in the composition profile where much of the para-xylene would be lost to the raffinate stream. The extract flush, shown at 22 in FIG. 1, is typically effected with the desorbent and is typically recycled as the feed flush stream 21.

In the system shown in FIG. 1, the contents of the transfer line previously used to remove the raffinate stream 14 from the adsorbent chamber 11 are flushed away from the adsorbent chamber 11 into the raffinate distillation column (not shown) used to separate the desorbent from the raffinate product. The flushing liquid is a stream 23 taken from the adsorbent chamber at an intermediate point between the entry point for the feed stream 13 and the withdrawal point for the raffinate stream 14. This flushing step is intended to eliminate the passage of raffinate material into the adsorbent chamber when the transfer line is subsequently used to deliver the feed stream 13 to the chamber 11.

Figure 2:
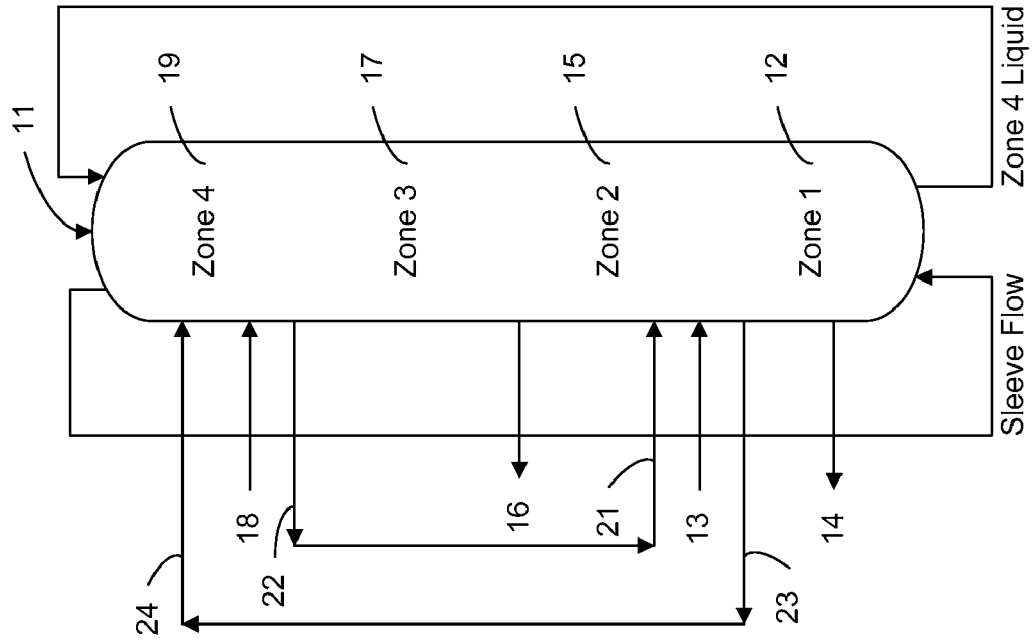
FIG. 2 is a schematic illustration of a simulated countercurrent adsorptive separation system according to one example of the invention.

A schematic representation of a simulated countercurrent adsorptive separation system according to one example of the invention is shown in FIG. 2. The basic construction and operation of the system of FIG. 2 is similar to that shown in FIG. 1 and hence like reference numerals are used in FIG. 2 to designate the same components as those in FIG. 1. However, in the system shown in FIG. 2, at least part the contents of the transfer line previously used to supply the desorbent stream 18 into the adsorbent chamber 11 are flushed into the chamber at a point along the column 11 between said transfer line just used to supply the desorbent stream 18 and the transfer line just used to withdraw the raffinate stream 14. The desorbent flush is shown at 24 in FIG. 2 and advantageously uses at least part of the raffinate flush 23 instead of feeding all the raffinate flush to the raffinate distillation column. Conveniently, the volume of liquid used for the desorbent flush is from about 0.5 to about 1 times, such as about 0.85 to about 0.95 times, the total volume of the transfer line and associated valving.

The process shown in FIG. 2 is advantageous in that it maximizes utilization of the desorbent and reduces the energy required to operate the raffinate distillation column. Thus, in a conventional simulated countercurrent adsorptive separation system, such as that shown in FIG. 1, approximately 5 to 10% by volume of the desorbent fed to the rotary valve(s) of the system never reaches the adsorbent chamber 11 but instead is retained in the transfer lines and recycled back to the raffinate distillation column. Since this additional desorbent is mixed with the raffinate stream 14, additional energy is required to fractionate the stream 14. By using the raffinate flush stream 23 as the desorbent flush, all of the desorbent that is supplied to the rotary valve(s) can be utilized in the separation process. Alternatively, if the volume of desorbent that reaches the adsorption chamber 11 is kept constant, the total desorbent flow can be reduced by 5 to 10%. Reducing the desorbent portion of the raffinate stream by 5 to 10% allows the energy required to operate the raffinate distillation column to be reduced by 2.5 to 5%.

Any suitable method can be used to feed the desorbent flush stream to the column 11, including the provision of additional valving or replacing the solid metal shaft of an existing rotary valve with a hollow core and feeding the desorbent flush stream through the hollow core.

Examples of adsorbents which may be used in the present process include non-zeolitic molecular sieves, such as carbon-based molecular sieves, and zeolitic molecular sieves, such as zeolites X and Y. For instance, X zeolites exchanged with barium or barium and potassium ions at their exchangeable sites, are known to be selective adsorbents for p-xylene recovery from xylene mixtures. Other suitable zeolitic molecular sieves are those having at least one pore system defined by a ten-membered ring of tetrahedrally coordinated atoms. Examples of suitable molecular sieves include those having a structure type selected from MFI, MEL, TON, MTT, MFS, MWW, FER, EUO, AEL, ITH and AFO.

$C_8$ aromatic feed mixtures which can be utilized in the present process are typically prepared by fractional distillation and comprise para-xylene and at least one other $C_8$ aromatic isomer, optionally with other hydrocarbons. Thus, the feed mixture can contain sizable quantities of $C_6$, $C_7$, and $C_9$ aromatics and may also contain quantities of straight or branched chain paraffins, cycloparaffins, or olefinic materials having boiling points relatively close to the desired xylene isomer. The desired xylene may be the para, meta or ortho isomer. The feed can alternatively contain a mixture of isomers of other aromatic or paraffinic hydrocarbons. Some specific examples are cresol isomers, cymene isomers and dimethyl naphthalene isomers. The subject process may also be employed to separate classes of compounds such as olefins from paraffins or straight chain paraffins from nonstraight chain; e.g., iso and cycloparaffins.

Mixtures containing substantial quantities of para-xylene, other $C_8$ aromatic isomers, and other hydrocarbons, such as $C_9$ aromatics, are generally produced by catalytic naphtha reforming and/aromatic hydrocarbon isomerization processes. These processes are well known in the refining and petrochemical arts. In a catalytic naphtha reforming process a naphtha boiling range feed is contacted with a platinum and halogen-containing catalyst at severities selected to produce an effluent containing $C_8$ aromatic isomers. Generally, the reformate is then fractionated to concentrate the $C_8$ aromatic isomers into a $C_8$ fraction which will also contain coboiling nonaromatics and some $C_7$ and $C_9$ aromatics. Feed mixtures for the present process may also be obtained from isomerization and transalkylation processes. For instance, the transalkylation of mixtures of $C_7$ and/or $C_9$ aromatics produces xylene isomers. Xylene mixtures recovered from the adsorption zone which are deficient in one or more isomers, such as from the raffinate stream 14, can be isomerized to produce an effluent containing an equilibrium distribution of $C_8$ aromatic isomers, which can then be recycled to the adsorption zone for separation of the para-xylene.

Benzene, toluene, and p-diethylbenzene are normally described as suitable desorbents for para-xylene recovery, with p-diethylbenzene (p-DEB) having become a commercial standard for the separation. P-DEB is a "heavy" desorbent (higher boiling than p-xylene) which allows for easier recovery of the desorbent from the extract and raffinate streams by fractional distillation.

Adsorption conditions in general include a temperature range of from about 20° C. to about 250° C., with from about 60° C. to about 200° C. being preferred for para-xylene separation. Adsorption conditions also include a pressure sufficient to maintain liquid phase, which may be from about atmospheric to 600 psig (100 to 4240 kPa). Desorption conditions generally include the same range of temperatures and pressure as used for adsorption.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the separation of a first chemical compound from a liquid feed stream comprising at least first and second chemical compounds by simulated countercurrent adsorptive separation, the process comprising:
   (a) passing the feed stream and a liquid desorbent stream into at least one multi-bed adsorbent chamber at two different points via different transfer lines;
   (b) removing an extract stream rich in said first chemical compound and a raffinate stream depleted in said first chemical compound from the adsorbent chamber at two different points by two additional transfer lines; and
   (c) flushing the contents of the transfer line which has just been used to supply the desorbent stream into the adsorbent chamber at a point along the chamber between said transfer line just used to supply the desorbent stream and the transfer line just used to withdraw the raffinate wherein the feed stream comprises a $C_8$ aromatics hydrocarbon stream and said first chemical compound comprises para-xylene.

2. The process of claim 1 and further comprising:
   (d) flushing the contents of the transfer line which has just been used to remove the raffinate stream from the adsorbent chamber and using at least part of the raffinate flush for said flushing (c).

3. The process of claim 2, wherein a stream from the adsorbent chamber at an intermediate point between the feed entry point and raffinate withdrawal point is used for the flushing (d).

4. The process of claim 1, wherein the volume of liquid used for said flushing (c) is from about 0.5 to about 1 times the total volume of said transfer line and associated valving.

5. The process of claim 1, wherein the volume of liquid used for said flushing (c) is from about 0.85 to about 0.95 times the total volume of said transfer line and associated valving.

* * * * *